(12) United States Patent
Zhang et al.

(10) Patent No.: US 10,004,713 B2
(45) Date of Patent: Jun. 26, 2018

(54) USES OF CHLOROGENIC ACID IN THE PREPARATION OF MEDICAMENTS FOR TREATMENT OF OLIGODENDROGLIOMA

(71) Applicant: SICHUAN JIUZHANG BIOLOGICAL SCIENCE AND TECHNOLOGY CO., LTD, Chengdu, Sichuan (CN)

(72) Inventors: Jie Zhang, Sichuan (CN); Lina Zhu, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days. days.

(21) Appl. No.: 15/518,193

(22) PCT Filed: Oct. 14, 2014

(86) PCT No.: PCT/CN2014/086536
§ 371 (c)(1),
(2) Date: Apr. 10, 2017

(87) PCT Pub. No.: WO2016/058116
PCT Pub. Date: Apr. 21, 2016

(65) Prior Publication Data
US 2017/0304250 A1    Oct. 26, 2017

(51) Int. Cl.
*A61K 31/216* (2006.01)
*A61K 9/00* (2006.01)

(52) U.S. Cl.
CPC .......... *A61K 31/216* (2013.01); *A61K 9/0019* (2013.01)

(58) Field of Classification Search
CPC ............................ A61K 31/216; A61K 9/0019
USPC ......................................................... 514/533
See application file for complete search history.

(56) References Cited

FOREIGN PATENT DOCUMENTS

CN         104188949 A      12/2014

OTHER PUBLICATIONS

Anissa Belkaid et al., "The Chemopreventive Properties of Chlorogenic Acid Reveal a Potential New Role for the Microsomal Glucose-6-phosphate Translocase in Brain Tumor Progression", Cancer Cell International, vol. 7, No. 6, Mar. 27, 2006.
Le Wang, "Extraction, Separation and Purification of Chlorogenic Acid from Acer Truncatum Bunge", Northwest University, Master's Dissertation, Apr. 2010.
Bathelemy Ngameni et al., "Inhibition of MMP-2 secretion from brain tumor cells suggests chemopreventive properties of a furanocoumarin glycoside and of chalcones isolated from the twigs of Dorstenia turbinate." Phytochemistry, vol. 67, Issue 23, Dec. 2006, pp. 2573-2579.

*Primary Examiner* — Kristin A Vajda
(74) *Attorney, Agent, or Firm* — Novick, Kim & Lee, PLLC; Allen Xue

(57) ABSTRACT

The present invention provides uses of chlorogenic acid in the preparation of medicaments for treatment of oligodendroglioma. Chlorogenic acid according to the present invention has an inhibitory action against oligodendroglioma, and can inhibit the growth of brain tumor stem cells, thus can partly substitute chemoradiation. Chlorogenic acid can alleviate the unwell response of patients caused by chemoradiation, and become a new medicinal therapeutic means and choose for treatment of oligodendroglioma.

5 Claims, 1 Drawing Sheet

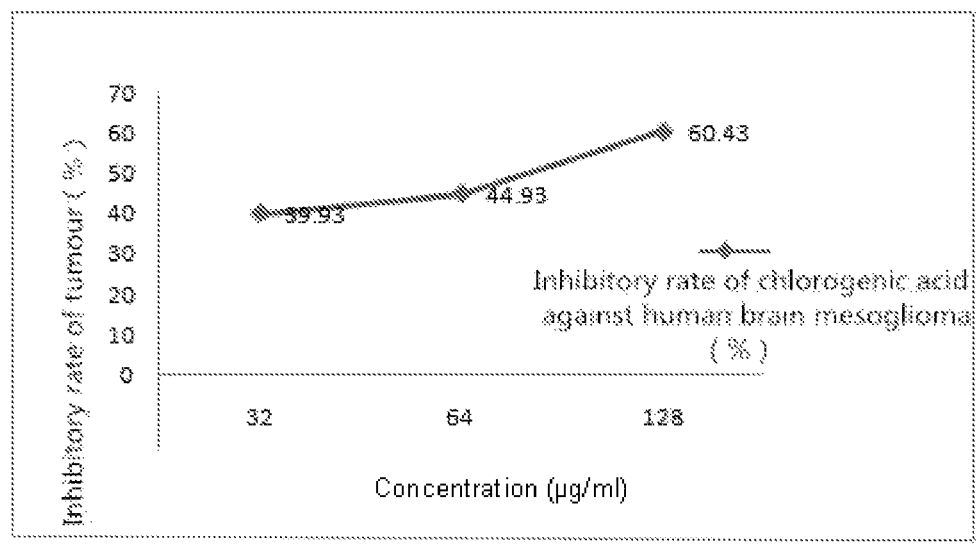

USES OF CHLOROGENIC ACID IN THE PREPARATION OF MEDICAMENTS FOR TREATMENT OF OLIGODENDROGLIOMA

TECHNICAL FIELD

The present invention relates to uses of chlorogenic acid in the preparation of medicaments for treatment of oligodendroglioma.

BACKGROUND ART

In recent years, the cancer mortality has become the first leading cause of death in China, that was probably related to smoke, the population aging, the industrialization process, etc. The incidence of common tumors such as esophageal cancer, stomach cancer, liver cancer and so on has remained in a constant high level in traditional poor zones, while the incidence of lung cancer, breast cancer, colonic cancer and so on has already fast increased in rich countries. The latest investigation indicated the incidence of brain neoplasm in developed countries was rising, and this disease further showed an evident low aging tendency, and gradually approached young people under 40 years-old, and became one of important tumors threatening children health. According to U.S. statistics, as far as the tumor death causes in 20~40 years-old people, brain neoplasm is the first leading cause in men, and the fifth leading cause in women, indicating the great harmfulness of brain neoplasm to public society. Nowadays, brain neoplasm is still one of first mortality cancers in adults, while is the solid tumor with highest incidence in children.

Neuroglioma, also called gliocytoma, is a common malignant tumor occurred in central nervous system, and arises from neuroepithelium and accounts for 40%~50% of all intracranial neoplasmas, which is characterized by high incidence rate, high recurrence rate, high fatality rate and low recovery rate. Based on the cell differentiation of glioma, glioma can be classified as astrocytoma, oligodendroglioma, ependymoma, etc, and its growth feature is infiltrative, without obvious margin with normal brain tissue. In general, its growth does not limit to one lobe of brain, and penetrates from inside brain tissues to the outside in finger-like shape, destroying brain tissues. At present, the main therapeutic measure for brain glioma is surgical ablation, but the 5-year survival rate is low. Glioma is not sensitive to radiotherapy and chemotherapy, thus, there is an urgent need for development of biological drugs used for its therapy.

There are many methods for classification of brain neoplasms, and currently, unified classification cannot be found. Moreover, histogenesis and pathologic characterization of various neoplasms are different, and their benign and malignancy as well as biological perperties are further not same. Astrocytoma, oligodendroglioma, and ependymoma differ from each other in many ways, and the specific difference is as follows:

1. Astrocytic tumor is a glioma consisted with astroglia cells, and as a most common refractory tumor, it accounts for 13%~26% of intracranial neoplasms and 21.2%~51.6% of neuroepithelial neoplasms. In gliomas, glioblastoma is the most common primary brain tumor, and the median survival of patients is merely about 15 months. Gelatinous membrane cell tumor shows invasive growth, and may extensively infiltrate into normal brain tissues, resulting in difficulty in surgical ablation; next, glioblastoma is resistant to general radiotherapy and chemotherapy, that is the important reason that it has high fatality rate and high recurrence rate. For its pathogenesis has not been fully interpreted, currently, effective therapeutic methods of brain glioblastoma is absent. Astrocytoma and oligodendroglioma are different in the expression level of RTN4. Expression of RTN4A in oligodendroglioma is obviously higher than that in astrocytoma, that is used for identifying the specificity and the sensitivity of oligodendroglioma.

2. Oligodendroglioma is a rarer neuroepithelium cancer, and usually found in adults, with an average age of onset being about 40 years old. In the past, due to limitation of examining techniques and pathological diagnosis level, it is easy for oligodendroglial tumor to escape diagnosis or be misdiagnosed, and literature indicates it accounts for 2%~5% of primary intracranial tumors, and 2%~12% of brain gliomas. But, in recent years, with the constant development of clinical research and the constant improvement of pathological diagnosis level, the detection rates of oligodendroglioma obviously increase, and literature reports it occupies about 33% of intracranial gliomas. Oligodendroglioma is an intracranial tumor arising from oligodendrocytes, and as an independent type of glioma, it accounts for 4.39% of intracranial tumors. In recent years, a great advance has been made in study on molecular genetics of oligodendroglioma, and the most common genetic change is the loss of heterozygosity on long arm of chromosome 19, while the second common genetic change is the loss of heterozygosity on short arm of chromosome 1. According to WHO newest classification of pathologic grading (2007), oligodendroglioma is classified as simple-type oligodendroglioma and mixed-type oligodendrocyte astrocytoma. The simple-type oligodendroglioma is further classified as low grade oligodendroglioma (Grade II), high grade oligodendroglioma (Grade III), and multiform glioblastoma (Grade IV); mixed-type oligodendrocyte astrocytoma is further classified as oligodendrocyte astrocytoma (Grade II) and anaplastic astrocytomas (Grade III). Recent investigation indicates low grade of oligodendrocyte tumors are more sensitive to chemotherapy, and different grade of oligodendrocyte tumors have obvious different clinical outcome and prognosis.

3. Ependymoma is a central nervous system neoplasm arising from ependymal cells in cerebral ventricles and spinal canal or ependyma cell nests of cerebral white matter. It accounts for 18.2% of gliomas, and is commonly seen in children and young, men much more than women. About 75% of ependymomasare below the tentorium, while 25% are above the tentorium. This tumor is extensively seen in cerebral ventricles, and a small number of tumor body in brain tissues. Ependymoma is a neuroepithelial neoplasm originating from ependymal epithelium cells, and may occur in intracalvarium and in spinal canal. It may spread along subarachnoid space, and at present, it is hard to completely cure it. Different pathologic types of gliomas have their respective high risk ages, and the high risk age of ependymoma is 10 years-old. Based on foreign statistics, 96% of ependymomasare seen in adults, and the high risk age is about 35~45 years-old. It is a most-common spinal cord neoplasm in adults, and about accounts for 34.5% of all ependymomas of central nervous system and 60% of intramedullary tumors and 75% of ependymomas in adults. Investigation has shown that for ependymomas, 50% of them lost the segment of chromosome 22, and that gene SV40 is closely related with ependymoma. According to the newest classification, ependymal tumors are classified as: (1) ependymoma: having four subtypes: ① cellular type; ② papillary type; ③ clear cell type; ④ tanycyte type. (2) anaplasia or malignant ependymoma: tumor cells are densely packed, with morphologically distinct cells and nucleus, as well as visible mitotic figures and necrosis areas. (3) myxo-papillary ependymoma: tumor cells are arranged in papillary shape, and connective tissues surrounding papillary structures have mucoid-appearing changes. (4) sub-ependymoma: most cells forming tumors are sub-ependymagliacytes, with visible pseudorosettes arrangement. Small amounts of ependymal cells and ependyma mother cells are sometimes distributed among gelatinous fibers. Ependymal tumors are not sensitive to chemotherapy, and in clinical trials, when various chemotherapeutic agents are administrated alone or together, the effect is weak.

Treatment of glioma is mainly by surgery, but for poor cell differentiation, rapid proliferation, strong invasiveness, current operation manner cannot completely remove tumors, and a combined modality therapy is generally accepted. Post operation radiotherapy and chemotherapy are the received therapeutic method, however, the radiation tolerance of tumor cells to radiotherapy probably causes the further recurrence of residual lesions. In addition, brain tumors are all not so reactive to chemotherapy, and one of reasons is that only a few drugs can pass through the blood-brain barrier. Because of blood-brain barrier, higher hydrostatic pressure of brain tissue spaces caused by edema of tumor tissues and their periphery, as well as other factors, the effective concentration of chemotherapeutic drugs in tumors is lower. Further, development of drug tolerance of tumors, adverse reaction of systemic administration and so on all have an effect on treatment effectiveness of chemotherapy. In order to improve therapeutic effect of gliomas, from molecular pathogenesis of glioma to new clinical therapeutic tools, people have done lots of work.

Chlorogenic acid widely exists in various medicinal plants, such as *Flos Lonicerae*, and nowadays, its structure has already been determined. Its medicinal uses have been investigated, and it is reported that chlorogenic acid can treat tumors and other diseases. At present, literature reporting that chlorogenic acid is used for treatment of glioblastoma mainly focuses on mechanism of action, such as reference "The chemopreventive properties of chlorogenic acid reveal a potential new role for the microsomal glucose-6-phosphate translocase in brain tumor progression" reports glucose-6-phosphotransferase (G6PT) in brain glioma cell lines U87 can regulate intra-cellular signaling pathway, and presents high expression state, that is closely related to invasion of tumor cells; chlorogenic acid can antagonize U87 cell migration induced by G6PT, and obviously inhibit U87 cell migration induced by sphingosine (SIP). It is proved that chlorogenic acid can achieve effects of inhibiting neoplasm metastasis by inhibiting activities of matrix metalloproteinase and glucose-6-phosphotransferase. Reference "Inhibition of MMP-2 secretion from brain tumor cells suggests chemopreventive properties of a furanocoumarin glycoside and of chalcones isolated from the twigs of Dorstenia turbinata" reports chlorogenic acid, as inhibitor of matrix metalloprotein transferase, can inhibit secretion of MMP-2, and realize to inhibit cell transfer of glioblastoma of brain tumors. Chlorogenic acid is an inhibitor of G6PT. That indirectly indicates effects of chlorogenic acid on brain neoplasms. But, G6PT mentioned in literature is a generalized carcinogen, and referred brain neoplasms are also a broad definition, that cannot show direct effects of chlorogenic acid on brain tumors. Le Wang (Extraction, isolation and purification of chlorogenic acid from *Acer truncatum*, Northwest University, Master's thesis 20100401) reports anticancer and anti-aging actions of chlorogenic acid, which discloses chlorogenic acid can inhibit metastasis of glioma as well as secretion of metallothionein (MMP) in human Hep3Bhepatoma carcinoma cells, and has significant therapeutic effects on large intestine cancer, liver cancer, and larynx cancer, thus it is regarded as an effective protective agent against cancers.

In summary, effects of chlorogenic acid on brain tumors reported by literature limit to glioblastoma, one type of astrocytomas (explaining in "mechanism of action"), without in vivo pharmacodynamic test verifying the use of chlorogenic acid for treatment of brain glioblastoma, as well as without related reports about the inhibitory action of chlorogenic acid on brain glioma stem cells.

CONTENT OF THE INVENTION

The technical solution provides new uses of chlorogenic acid.

Uses of chlorogenic acid of the present invention in the preparation of medicaments for treatment of oligodendroglioma.

Wherein, said medicament is those having an inhibitory action on transplanted brain glioma.

Wherein, said medicament is those having an inhibitory action on the growth of C6 glioma cells.

Wherein, said medicament is those having an inhibitory action on the growth of C6 glioma stem cells.

Wherein, said medicament is prepared by an effective amount of chlorogenic acid as active ingredient, together with pharmaceutically acceptable adjuvants or auxiliary ingredients.

Wherein, said pharmaceutical preparation contains 1~3000 mg chlorogenic acid per preparation unit.

Further, in said pharmaceutical preparation, the dosage of chlorogenic acid used is 10~40 mg/kg.

Further preferably, in said pharmaceutical preparation, the dosage of chlorogenic acid used is 20 mg/kg.

Wherein, said medicament is oral preparations or injections.

Although literature reports chlorogenic acid can antagonize U-87 glioblastoma metastasis induced by over-expression of recombinant G6PT protein in in vitro experiment, literature only indicates effects of chlorogenic acid on glucose-6-phosphotransferase during brain tumor progression, and does not directly demonstrate that chlorogenic acid has actions against U-87 glioblastoma; and chlorogenic acid inhibits transfer of U-87 human glioblastoma, belonging to glioblastoma, but glioblastoma and oligodendroglima, ependymoma are different types of gliomas and different indications. Thus, these evidences cannot deduce that chlorogenic acid has inhibitory effects on oligodendroglima and ependymoma.

For glioblastoma, oligodendgroglioma, and ependymoma, their etiology, histopathology, and clinical aspects are obviously different. Ependymoma is a neuroepithelial neoplasm originating from ependymal epithelium cells, and may occur in intracalvarium and in spinal canal. It may spread along subarachnoid space, and at present, it is hard to completely cure it. Based on foreign statistics, 96% of spinal ependymoma is seen in adults, and the high risk age is about 35~45 years-old. Ependymoma is a most-common spinal cord neoplasm in adults, and about accounts for 34.5% of all ependymomas of central nervous system and 60% of intramedullary tumors and 75% of ependymomas in adults. According to WHO newest classification (2000), ependymal tumors are classified as: (1) ependymoma: having four subtypes: ① cellular type; ② papillary type; ③ clear cell type; ④ tanycyte type. (2) anaplasia or malignant ependymoma: tumor cells are densely packed, with morphologically distinct cells and nucleus, as well as visible mitotic figures and necrosis areas. (3) myxo-papillary ependymoma: tumor cells are arranged in papillary shape, and connective tissues surrounding papillary structures have mucoid-appearing changes. (4) sub-ependymoma: most cells forming tumors are sub-ependymagliacytes, with visible pseudorosettes arrangement. Small amounts of ependymal cells and ependyma mother cells are sometimes distributed among gelatinous fibers. Currently, for ependymoma without spreading via cerebrospinal fluid, the treatment way is trying the best to gain total resection of tumor by surgery, with aid of postoperative local radiotherapy, that may provide the best therapeutic effect. But, it seems that whether traditional combination chemotherapy or large-dose chemotherapy cannot improve prognosis, although some experimental results show tumors are sensitive to chemotherapy.

Oligodendroglioma is a rarer neuroepithelium cancer, and literature indicates it accounts for 2%~5% of primary intracranial tumors, and 2%~12% of brain gliomas. But, in recent years, with the constant development of clinical research and the constant improvement of pathological diagnosis level, the detection rates of oligodendroglioma obviously increase, and literature reports it occupies about 33% of intracranial gliomas. According to WHO newest classification of pathologic grading (2007), oligodendroglioma is classified as simple-type oligodendroglioma and mixed-type oligodendrocyte astrocytoma. The simple-type oligodendroglioma is further classified as low grade oligodendroglioma (Grade II), high grade oligodendroglioma (Grade III), and multiform glioblastoma (Grade IV); mixed-type oligodendrocyte astrocytoma is classified as oligodendrocyte astrocytoma (Grade II) and anaplastic astrocytomas (Grade III). Recent investigation indicates low grade of oligodendrocyte tumors are more sensitive to chemotherapy, and different grade of oligodendrocyte tumors have obvious different clinical outcome and prognosis.

Chlorogenic acid of the present invention has inhibitory effects on oligodendroglioma, and can inhibit the growth of C6 glioma stem cells, thus can partly substitute chemoradiation. Chlorogenic acid may alleviate the unwell response of patients caused by chemoradiation, and become a new medicinal therapeutic means and choose for the treatment of oligodendroglioma.

DESCRIPTION OF FIGURES

FIG. 1. Dose response curve of chlorogenic acid against human brain oligodendroglioma.

EXAMPLES

In the following text, the beneficial effect of the present invention is proved by specific pharmacodynamic experiments.

Hereinafter, the present invention can further be illustrated with reference to following figures and examples, in order to better understand the purpose and the advantage of the present invention. But it should not be understood that above subject scope of the present invention is limited to the following examples. The technology that can be realized based on above contents of the present invention should all be within the scope of the present invention.

Example 1 Experimental Study of Chlorogenic Acid Inducing Apoptosis of Human Oligodendroglioma 1. Materials Cells: Human oligodendroglioma cells are obtained from Key Laboratory of Transplant Engineering and Immunology, Ministry of health, West China Hospital, Sichuan University.

Drugs and reagents: Chlorogenic acid is provided by Sichuan Jiuzhang Bio-chemical Science and Technology Development, Co. Ltd; Glutamic acid is purchased from Zhejiang Tianrui Chemical Co. Ltd; Methyl thiazolyl tetrazolium (MTT), 0.25% trypsin, RPMI1640 culture solution and fetal bovine serum are all from Sigma (USA).

2. Methods 2.1 Primary Culture of Human Brain Oligodendrocytes (1) Primary Culture Sterile fresh tumor samples (human brain oligodendroglioma) removed by operation were immediately placed in culture solution and sent to laboratory. The samples were washed with serum-free RPMI-1640 containing penicillin, streptomycin, and gentamicin for 2~3 times, to move blood of samples. Purer tumor tissues were selected under a microscope, and moved to an aseptic penicillin bottle. Necrotic tissue and blood vessels and similar structures were trimmed, and tumor tissue pieces were taken out and cut into small pieces of 0.5~1 $mm^3$, to which was added 1~2 mL cell culture fluid. The culture was gently blown using a pipette, to make tissue pieces to suspense. Suspension of tissue pieces was suctioned using an pipette for several times, and uniformly arranged on the bottom of culture bottle. The bottle was inversed, and 2~3 mL culture solution was added, then cultured for 2~3 h in an incubator containing $CO_2$ at 37° C. After tissue pieces were firmly attached to the plane, the culture bottle was slowly turned over, that allowed tissue pieces to immerse in culture solution, for continuous culture.

(2) Passage of Primary Cells

After cells covered the bottle bottom, the culture solution was poured out, and then washed once with serum-free RPMI1640. 0.25% trypsin was added and digested for 5 min, followed by stopping digestion with culture solution containing serum. After repeatedly blowing up, cells were collected and counted, then seeded in 25 $cm^2$ culture bottle at a density of $5\times10^4$ cells/$cm^2$ for serial sub cultivation.

(3) Observing Morphology of Human Brain Oligodendroglioma Cells

Morphology of primary culture cells was observed under inverted phase contrast microscope. To culture cells, was added 1 mL Hank's solution containing 5 µmol/L Fluo-3/AM fluorescent probe and 5 µmol/L Pluronic F-127, then incubated at 37° C. for 40 min, that was washed three times with Hank's solution without fluorescent probe. Loaded cell solution was placed under confocal laser scanning microscope to observe cellular state, and by comparing with pathologic examination results of primary operation, cells were determined as human brain oligodendroglioma cells. Culture cells were further confirmed by immunohistochemistry of glial fibrillary acidic protein.

(4) Detecting Inhibitory Effects of Chlorogenic Acid on Proliferation of Primary Culture Cells of Human Brain Mesoglioma by MTT Method Inoculation of cells: cells in exponential phase of growth were taken out, digested with 0.25% trypsin, washed with basal medium, and centrifuged (1000 rpm, each for 5 min, twice). Cells were suspended in complete medium, and the concentration was adjusted as $6\times10^4$/ml. Cells were inoculated in 96 well plate, 50 µl for each well ($6\times10^3$ cells/well). Three replicates were made for each concentration of drug, and normal control group (tumor cells+complete medium) and blank control group (complete medium) were included, each group with three repeat holes.

Addition of drug: Next day after inoculation, drug was added in below groups following by cell adherence. For chlorogenic acid group, 256 µg/ml of chlorogenic acid solution was prepared by diluting 6.4 mg/ml stock solution with complete medium, then diluted with complete medium using two-fold dilution way, to obtain complete medium containing 256, 128, 64 µg/ml of chlorogenic acid for use; 50 µl of above complete medium containing different concentrations of chlorogenic acid was added to 96 well plate inoculated cells, with a final concentration of chlorogenic acid being 128, 64, 32 µg/ml, three replicates for each concentration. 48 h static culture was performed; for blank control group, cells were not inoculated in each well, and only equal amount of complete medium was added, with three wells for blank group.

Determination: After addition of drug, cells were cultured for 48 h, and to three experimental groups and blank control group mentioned above, was added 10 μl WST-1 solution. The plate was placed in a cell incubator at 37° C. for 4 hours, and absorption values of different drug groups, normal control group, and blank control group were determined at 440 nm using μ-Quantmicrotiter plate determinator.

Data processing: calculating growth inhibitory rate of tumor cells:

Inhibitory rate=($A$ value of control group−$A$ value of experimental group)/$A$ value of control group× 100%. Experiment was repeated thrice.

3. Experimental Results
3.1 In Vitro Inhibitory Effect of Chlorogenic Acid on Human Brain Oligodendroglioma
(1) Observation Results of Cellular Morphology After each group was treated with drug for 48 h, cellular morphology was observed under inverted microscope, and by comparison with normal control group, low concentration of chlorogenic acid (32~128 m/ml) showed obvious decrease of cell numbers comparing with normal cells, accompanied by cell fragments and apoptosis.
(2) Inhibitory Rate of Chlorogenic Acid Against Human Brain Oligodendroglioma and the Dose Response Curve Inhibitory rate of chlorogenic acid against human brain oligodendroglioma is shown in Table 1, and the dose response curve is shown in FIG. 1.

TABLE 1

Inhibitory rate of chlorogenic acid against human brain oligodendroglioma

| Group | | 1 | 2 | 3 | mean | Inhibitory rate (%) |
|---|---|---|---|---|---|---|
| Chlorogenic acid group | 32 | 1.057 | 1.745 | 0.732 | 1.178 | 39.93 |
| | 64 | 0.705 | 1.147 | 1.388 | 1.080 | 44.93 |
| | 128 | 0.333 | 0.536 | 1.459 | 0.776 | 60.43 |
| Normal control group | | 2.687 | 1.654 | 1.542 | 1.961 | — |

After treatment with 32, 64, and 128 m/ml of chlorogenic acid for 48 h, the inhibitory rate curve against primary culture cells is shown in FIG. 1. As increase in action concentration of chlorogenic acid, the inhibitory effect on oligodendroglioma cells is more obvious. It can be seen that inhibition of chlorogenic acid against primary culture cells of human brain oligodendroglioma presented obvious dose-effect relationship.

4. Conclusion

In vitro experiment on inhibition of chlorogenic acid against tumors showed chlorogenic acid has inhibitory action on human brain oligodendroglioma. Above experiment proved chlorogenic acid of the present invention has inhibitory effects on human brain oligodendroglioma, can partly substitute chemoradiation. Chlorogenic acid may alleviate the unwell response of patients caused by chemoradiation, and become a new medicinal therapeutic means.

Example 2 Investigation on Inhibitory Effect of Chlorogenic Acid on Transplanted Glioma 1. Materials
Materials: Human brain glioma cell lines are provided by Key Laboratory of Transplant Engineering and Immunology, Ministry of health, West China Hospital, Sichuan University. Chlorogenic acid is provided by Sichuan Jiuzhang Bio-chemical Science and Technology Development, Co. Ltd.

2. Methods
(1) Model establishment 50 mice were divided into 5 groups, 10 mice for each group. The solution of brain glioblastoma cell lines was suitably diluted, and inoculated in cortex of left temporal lobe of mice in five groups, respectively.
(2) Administration and intervention After inoculated for 24 h, five groups of mice were administrated by intraperitoneal injection. Five groups were high (40 mg/kg), middle (20 mg/kg), low (10 mg/kg) doses of chlorogenic acid and positive control docetaxel (5 mg/kg) respectively, and model group receiving same volume of normal saline, and mice were successively administered for 15 d.
(3) Measuring inhibitory rate On the last day, administration was ceased, and all mice were sacrificed. Mice were dissected, and tissue of tumor was removed and weighed.

Inhibitory Rate=(the Mean Tumor Weight of Control Group−the Mean Tumor Weight of Treatment Group)/the Mean Tumor Weight of Control Group×100%.

(4) Statistical method The data were presented as mean±standard deviation (x±s), and statistical analysis was performed using SPSS15.0 software, and $p<0.05$ was considered to be a statistically significant difference.

3. Results
Analytic result showed that the inhibitory rate of treatment group had a trend of obvious promotion, compared with blank group, confirming chlorogenic acid had an effect on growth of tumor. The inhibitory effect of middle dose group was most significant, followed by high dose group, and specific data were given in Table 2.

TABLE 2

Effects of chlorogenic acid on tumor weight and the inhibitory rate of human brain glioma($\bar{x} \pm s$)

| Group | Dose (mg/kg) | Tumor weight (g) | Inhibitory rate (%) |
|---|---|---|---|
| Blank control group | — | 1.341 ± 0.299 | — |
| Positive control group | 5 | 0.389 ± 0.305** | 73.3 |
| High dose group of chlorogenic acid | 40 | 0.529 ± 0.168** | 60.58 |
| Middle dose group of chlorogenic acid | 20 | 0.403 ± 0.101** | 69.92 |
| Low dose group of chlorogenic acid | 10 | 0.690 ± 0.188** | 48.51 |

4. Conclusion

In vivo experiment on inhibition of chlorogenic acid against tumors showed chlorogenic acid has inhibitory action on human brain glioma. Above experiment proved chlorogenic acid of the present invention has inhibitory effects on human brain glioma, can partly substitute chemoradiation. Chlorogenic acid can alleviate the unwell response of patients caused by chemoradiation, and become a new medicinal therapeutic means.

Example 3 In Vitro Experimental Study on Effect of Chlorogenic Acid Against C6 Glioma Stem Cells I. Drugs and Main Reagents and Materials
1. Powder injection of chlorogenic acid, with a purity of 99%, is provided by Sichuan Jiuzhang Bio-chemical Science and Technology Development, Co. Ltd., and its molecular weight is 354.

2. Main apparatus: Super clean bench, $CO_2$ constant temperature and humidity incubator, various micropipettors, electrically heated distilling apparatus, Quartz double distiller, culture dish, optical microscope, ultra cold freezer, size centrifuge, electro heat pressure steam sterilizer, constant temperature oven, flow cytometer, electronic microbalance and so on.

3. Cell line: C6 rat glioma cell lines for experiment is provided by Key Laboratory of Transplant Engineering and Immunology, Ministry of health, West China Hospital, Sichuan University.

II. Experimental Procedures (I) Cell Recovery and Inoculation

1. Cell Recovery (1) Indoor UV disinfection; culture medium and PBS were preheated on thermostatic water bath at 37° C. for use.

(2) Safety glasses and gloves were worn, and frozen pipes containing C6 cells were taken out from nitrogen canister, that were fast placed in enamel jar at 36° C.~37° C., followed by occasionally shaking, to make a quick thawing.

(3) Bandage pocket was scissored, and ampules were brought out, then cleaned and polished with 70% alcohol to disinfect. On super clean bench, the cap of frozen pipe was removed, and suspension of cells was suctioned with pipette, and transferred to centrifuge tube. 8 ml of pre-warmed DMEM/F12 culture solution containing 10% fetal bovine serum was added, and then pipetted to make a cell suspension.

(4) 5 min low speed centrifugation (500-1000 rpm) was performed, and supernatant was drawn out and washed repeatedly with PBS, then centrifugated.

(5) Suitable dilution was completed by addition of culture solution, and then transferred to culture bottles, stored in incubator at 37° C. in humidified air containing 5% $CO_2$. Recovery date was recorded, and next day, culture solution was changed for continuous culture.

2. Frozen Reservation of Cells (1) Preparation of cells: C6 glioma cells in exponential phase of growth were chosen, collected after changing culture solution once. Cells were digested with 0.25% trypsin and gently triturated to prepare single cell suspension, with a density of $1\times10^5$/ml, then centrifuged for 8 min(800 rpm).

(2) Preparation of freezing solution: 9 volumes of culture solution were combined with one volume of dimethyl sulfoxide (DMSO), to prepare 10% DMSO freezing solution.

(3) The freezing solution was slowly added to centrifuge tubes containing cell precipitate, and pipetted with pipettes, to make cells to suspense.

(4) Cell suspension was divided into frozen tubes, and then sealed.

(5) Cryopreservation: Frozen tubes were placed at −4° C. and kept for 2 h, then −20° C. for 2 hours, then −80° C. overnight. After that, tubes were stored in nitrogen canister.

3. Cultivation and Passage of C6 Cells (1) Cell growth state was closely observed, and when cells covered about 80-90% bottom of bottle, sub-culture was carried out;

(2) Culture bottles were brought out from the incubator at 37° C. with 5% $CO_2$. On super clean bench, the culture solution in bottles containing dense monolayer cells was discarded;

(3) 0.25% solution of pancreatin was added, and the amount is 0.5 ml or more that can be varied according to the size of cell bottles, in order to completely wet cells, and the digestion time is about 1~3 min. Semitransparent cell layer on the wall of bottle was visually observed, and once vacant space with a size of thin needle was seen, pancreatin solution was discarded, then suitable amount of cell culture solution was added to stop digestion;

(4) Low speed centrifugation (500-1000 rpm) was kept for 5 min, and supernatant was discarded, to which DMEM/F12 culture solution was added and gently pipetted to form cell suspension. In a ratio of 1:3, the cell suspension was divided and stored in culture bottles with a bottom area of 75 $cm^2$ for continual culture.

4. Cultivation and Passage of Glioma Stem Cells of C6 Cell Lines (1) C6 cells were seeded in traditional serum medium and sub-cultured in culture bottle. Cells in exponential phase of growth were washed with PBS solution, digested with 0.25% trypsin, and pipetted by self-made pasteur pipette, to form single cells. Cells were resuspended in SFM, stained with trypan blue, and counted. Cells were seeded in culture bottle with a bottom area of 25 $cm^2$ at a concentration of $1\times10^5$/well, and placed in an incubator at 37° C. with 5% $CO_2$ and saturated humidity for culture.

(2) After seeding cells in SFM, according to proliferative rate and size of C6 GSC, if monoclonal cell dumps suspended in the medium had a regular shape and a bigger volume (generally 4~5 days), cell dumps, together with medium, are transferred into test tubes on super clean bench, and adherent cells on the bottom were discarded. The medium was sucked out and centrifuged before half of old medium was removed, then centrifuged at 800 rpm/min for 5 min. The supernatant was discarded. Cells are resuspended in SFM, and gentle pipette with self-made pasteur pipette was repeated, for dissociating cell dumps into single cells. In a ratio of 1:2 or 1:3, cells were seeded in culture bottles with a bottom area of 25 $cm^2$, and diluted with SFM to 6 ml; alternatively, at the same concentration, cells were seeded in 6 well plate. To each well, was added 2.5 ml SFM, and continued culturing in an incubator at 37° C. with 5% $CO_2$ and saturated humidity.

5. Induction and Differentiation of Glioma Stem Cells of C6 Cell Lines

In SFM, one day after the third passage of C6 GSC was formed, C6 GSC or dispersed single cells were washed with D-Hanks solution, and resuspended in SSM. C6 GSC was seeded in 6 well plate at a concentration of $1\times10^5$/well. Everyday, the conditions of differentiation and growth were observed.

(II) Detecting In Vitro Inhibitory Effects of Chlorogenic Acid Against C6 Glioma and C6 Glioma Stem Cells by MTT Method (Three Separated Experiments)

(1) Cells, growing in serum-containing medium and serum-free medium and presenting exponential growth phase, were taken out, and digested with pancreatin, to form single cells. Tumor cells were still seeded in serum-containing medium, while tumor stem cells were seeded in serum-free medium. Their concentrations were both adjusted to $2.0\times10^5$/ml, and cells were seeded in 96 well plate, 100 μl for each well. Amongst, four groups were experimental groups, and one group was negative control; the medium without cells was used as blank control, and each group had five repeated wells. Culture was carried out in an incubator at 37° C. with 5% $CO_2$ and saturated humidity for one night. When seeding in 96 well plate, peripheral wells were not used to avoid the edge effect.

(2) Next day after inoculation, cells attached before administration was carried out and static culture was kept for 48 h. 6.4 mg/ml stock solution of chlorogenic acid was diluted to 256 μg/ml with complete medium, then diluted with complete medium using two-fold dilution way, to obtain complete medium containing 256, 128, 64, and 32 μg/ml of chlorogenic acid for use; 50 μl of above complete medium containing different concentrations of chlorogenic acid was added to 96 well plate containing inoculated cells, with a final concentration of chlorogenic acid being 128, 64, 32 μg/ml, three replicates for each concentration.

(3) Wells for normal control group of tumor cells were included, and the wells were not treated with drug, and only equal amount (100 μl) of complete medium was added. Experiment on normal control group was performed, together with above three groups.

(4) The culture was continued under 5% $CO_2$ at 37° C., and after culturing for 48 h, cells were placed under inverted microscope for observation and taking a picture.

(5) On sterile bench board, 20 μL 0.5% MTT was added to each well, and the culture was continued for 4 h. At 37° C., the culture was stood for overnight (same time for each group), then OD values were tested using microplate reader, while the absorbance of each well was measured at 440 nm.

(6) Calculating inhibitory rate of cell growth

Formula: Inhibitory rate of cell growth IR (%)=1−(OD value of cells in experimental group/OD value of cells in control group)×100%.

(III) Statistical Analysis

The experimental results were presented as mean±standard deviation (x̄±s), and results were analyzed with analysis of variance. Statistical analysis was performed using SPSS13.0 software. Size of test: $P<0.05$ was considered to be a statistical difference, while $P<0.01$ was considered to be statistically significant difference.

III. Experimental Results (I) Results of Cell Culture

1. Culture of C6 Glioma Cells

In serum-containing medium, a part of cells grew with adherence after a few hours, and after 24 h, adherent cells could be seen with a larger nucleus, abundant cytoplasm, adherent growth of cells, processes; after 48 h, cells extended processes and formed network structure, i.e. forming single layer of adherent cells. On the third day, adherent cells covered about 80% bottom of culture plate.

2. Culture of C6 Glioma Stem Cells

C6 cells at exponential growth phase were selected and seeded in serum-free medium, and after 24 h, cells presented single cell, and homogeneous distribution and scattered adherence were seen. A few cells aggregated and began to produce globoferous cells suspended in medium, similar to neural stem cell spheres, and cell spheres suspended and grew, formed spherical or ovoid shapes, with different sizes and strong refraction; Other cells precipitated in bottom of culture plate, and presented single cell growth. On the third day, dozens of cells presented spherical suspension growth, and spherical cell dumps could be seen. On the fifth and seventh days, it could be seen that cell spheres further grew and became larger.

3. Culture of C6 Glioma Stem Cells after Induction and Differentiation in Serum-Containing Medium Suspension cell spheres were seeded in medium containing 10% fetal bovine serum, and after 24 h, cell spheres began to attach and form processes; after 48 h, cell numbers increased and formed a small piece of cell island; On the third day, cell islands enlarged and adjacent cell islands mixed together, and cells presented adherent growth; On the seventh day, adherent cells grown well were seen, and they covered about 60% bottom of culture plate.

(II) Experimental Results of In Vitro Inhibitory Rate of Chlorogenic Acid

Effect of various concentrations of chlorogenic acid on two kinds of cells was determined by MTT method, and OD values were obtained to calculate inhibitory rate against cells. Results showed as concentrations of chlorogenic acid increasing, the inhibitory rate of each experimental group against both kinds of cells also successively improved.

TABLE 3

OD values and inhibitory rates of chlorogenic acid against C6 glioma cells and C6 glioma stem cells.

| Groups | | OD values | | | | Inhibitory rate (%) |
|---|---|---|---|---|---|---|
| | | 1 | 2 | 3 | mean | |
| C6 glioma | 16 | 1.640 | 1.553 | 1.351 | 1.515 | 32.14 |
| | 32 | 1.558 | 1.573 | 1.286 | 1.472 | 34.04 |
| | 64 | 1.314 | 1.247 | 1.417 | 1.326 | 40.59 |
| | 128 | 1.021 | 1.023 | 1.041 | 1.028 | 53.93 |
| | Blank control | 2.285 | 2.203 | 2.208 | 2.232 | — |
| C6 glioma stem cells | 16 | 1.713 | 1.700 | 1.731 | 1.715 | 23.18 |
| | 32 | 1.533 | 1.739 | 1.631 | 1.634 | 26.78 |
| | 64 | 1.367 | 1.358 | 1.410 | 1.378 | 38.25 |
| | 128 | 1.393 | 1.200 | 1.077 | 1.223 | 45.19 |
| | Blank control | 2.687 | 1.654 | 1.542 | 1.961 | — |

IV. Conclusions

In vivo experiment on effects of chlorogenic acid against C6 glioma stem cells showed it had inhibitory action on growth of C6 glioma cells and C6 glioma stem cells, while its inhibition on tumor stem cells is weaker. Above experiment proved chlorogenic acid of the present invention had inhibitory effects on human brain glioma, and can inhibit the growth of brain tumor stem cells, and become a new therapeutic means for human brain glioma.

The invention claimed is:

1. A method for treating oligodendroglioma, comprising: applying a pharmaceutical preparation to a patient in need thereof, wherein the pharmaceutical preparation comprises an effective amount of chlorogenic acid as active ingredient and pharmaceutically acceptable adjuvants or auxiliary ingredients.

2. The method according to claim 1, wherein the pharmaceutical preparation comprises 1-3000 mg chlorogenic acid per preparation unit.

3. The method according to claim 1, wherein a dosage of chlorogenic acid is 10-40 mg/kg.

4. The method according to claim 1, wherein the dosage of chlorogenic acid is 20 mg/kg.

5. The method according to claim 1, wherein the pharmaceutical preparation is an oral preparation or an injection.

* * * * *